(12) United States Patent
Shelling (10) Patent No.: US 6,787,311 B1
(45) Date of Patent: Sep. 7, 2004

(54) DIAGNOSIS OF PREMATURE OVARIAN FAILURE

(75) Inventor: Andrew N. Shelling, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 09/913,524

(22) PCT Filed: Feb. 25, 2000

(86) PCT No.: PCT/NZ00/00021

§ 371 (c)(1),
(2), (4) Date: Aug. 15, 2001

(87) PCT Pub. No.: WO00/50638

PCT Pub. Date: Aug. 31, 2000

(30) Foreign Application Priority Data

Feb. 25, 1999 (NZ) ................................. 334386

(51) Int. Cl.[7] .............................. C12Q 1/68; C12Q 1/44; C12P 19/34; C07H 21/04; C07K 14/435
(52) U.S. Cl. ............................ 435/6; 435/19; 435/91.5; 435/91.51; 536/23.5; 536/25.32; 530/350; 436/89
(58) Field of Search ............................ 435/6, 19, 91.5, 435/91.51; 536/23.5, 25.32; 530/350; 436/89

(56) References Cited

U.S. PATENT DOCUMENTS

| | | |
|---|---|---|
| 5,525,488 A | 6/1996 | Mason et al. |
| 5,665,568 A | 9/1997 | Mason et al. |
| 5,725,858 A | 3/1998 | Fioretti et al. |

FOREIGN PATENT DOCUMENTS

| | | |
|---|---|---|
| EP | 0 222 491 | 5/1987 |
| WO | WO 86/06076 | 10/1986 |
| WO | WO 87/05702 | 9/1987 |
| WO | WO 95/04931 | 2/1995 |
| WO | WO 96/40219 | 12/1996 |

OTHER PUBLICATIONS

Petraglia, F. et al. Low levels of serum inhibin A and inhibin B in women with hypergonadotropic amenorrhea and evidence of high levels of activin A in women with hypothalamic amenorrhea. Fertility and Sterility 70(5):907–912 (Sep. 1998), abstract only.*
Petraglia, F. et al. Low levels of serum inhibin A and inhibin B in women with hypergonadotropic amenorrhea and evidence of high levels of activin A in women with hypothalamic amenorrhea. Fertility and Sterility 70(5):907–912 (Nov. 1998).*
Stewart, A.G. et al. Human inhibin genes: genomic characterisation and sequencing. FEBS Letters 206(2):329–334 (Oct. 1986).*
Shelling, A.N. et al. Inhibin: a candidate gene for premature ovarian failure. Human Reproduction 15(12):2644–2649 (Dec. 2000).*
Marozzi, A. et al. Mutation analysis of the inhibin alpha gene in a cohort of Italian women affected by ovarian failure. Human Reproduction 17(7):1741–1745 (Jul. 2002).*
Buckler, H.M., et al; "Gonadotropin, steroid, and inhibin levels in women with incipient ovarian failure during anovulatory and ovulatory rebound cycles," *Journal of Clinical Endocrinology & Metabolism,* 72, pp. 116–124, (1991).
Burger, H.G., et al; "Serum inhibins A and B fall differentially as FSH rises in perimenopausal women," *Clinical Endocrinology,* 48, pp. 809–813, (1998).
Halvorson, L.M., et al; "Inhibin, activin, and follistatin in reproductive medicine," *Fertility & Sterility,* 65, pp. 459–469, (1996).
Hofmann, G.E., et al; "Inhibin–B—the physiologic basis of the clomiphene citrate challenge test for ovarian reserve screening"; *Fertility & Sterility,* 69, pp. 474–477, (1998).
MacNaughton, J., et al; "Age related changes in follicle stimulating hormone, luteinizing hormone, oestradiol and immunoreactive inhibin in women of reproductive age," *Clinical Endocrinology,* 36, pp. 339–345, (1992).
Pampfer, S., et al; "Clinical value of inhibin in women", *Journal de Gynecologie, Obstetrique et Biologie de la Reproduction,* 18, pp. 279–287, (1989), abstract only.
Reame, N.E., et al; "Net increase in stimulatory input resulting from a decrease in inhibin B and an increase in activin A may contribute in part to the rise in follicular phase follicle–stimulating hormone of aging cycling women," *Journal of Clinical Endocrinology & Metabolism,* 83, pp. 3302–3307, (1998).
Richardson, S.J., et al; "Follicular depletion during the menopausal transition: evidence for accelerated loss and ultimate exhaustion", *Journal of Clinical Endocrinology & Metabolism,* 65, pp. 1231–1237, (1987).
Burger, H., "Experimental Gerontology"; 35 pp. 33–39, (2000).
Welt, C. K., "Female reproductive aging is marked by decreased secretion of dimeric inhibin"; *Journal of Clinical Endocrinology & Metabolism;* 84(1); pp. 105–111, (1999).
Soules, M.R., "Inhibin and reproductive aging in women"; *Maturitas;* 30(2); pp. 193–204; (1998).
Miyamoto Kaoru et al; "Inhibin and Antibody Thereof"; JP1985000069209; Oct. 14, 1986; (JP61229826A2) abstract.

* cited by examiner

*Primary Examiner*—Diana B. Johannsen
(74) *Attorney, Agent, or Firm*—Nixon & Vanderhye (57) ABSTRACT

Methods by which a predisposition to Premature Ovarian failure (POF) can be determined. In particular, methods are provided for detecting whether a female has a predisposition to POF with reference to an alteration (mutation) in the gene coding inhibin.

7 Claims, 5 Drawing Sheets

INHα Wildtype

Figure 2a

INHα Variant

INHβA Wildtype

Figure 2b

INHβA Variant

DIAGNOSIS OF PREMATURE OVARIAN FAILURE

This invention relates to methods by which a predisposition to premature ovarian failure can be detected as well as to methods of diagnosis of premature ovarian failure. Still further, this invention relates to methods of therapy.

BACKGROUND

Premature ovarian failure (POF) is a condition causing secondary amenorrhea, hypoestrogenism, and elevated gonadotrophins in women younger than 40 years. POF will occur in 1% of women before the age of 40 years and in 0.1% or 1 in 1000 women before the age of 30 years (Coulam, Adamson et al. 1986). POF can be familial, genetically inherited, or sporadic where there has been no family history of the disorder. Even though there have been many advances into the cause of POF in the last few years, especially in the field of molecular genetics, the cause of POF in most cases remains a mystery. Most women presented with idiopathic POF have normal menstrual history, age of menarche, and fertility prior to the onset of the condition. It was once thought that POF was irreversible in all cases as in menopause, however, intermittent ovarian failure has been reported, and pregnancy can occur in approximately 10% of patients subsequent to diagnosis.

The most immediate concern for women with POF is the menopausal symptoms they experience due to the decrease in circulating oestradiol coupled with the psychological implications of these symptoms. The menopausal symptoms include hot flushes, night sweats, insomnia, palpitations, headaches, incontinence, and dyspareunia as a result of vaginal dryness. The psychological implication of POF not only include those associated with menopause such as forgetfulness, poor concentration, irritability and mood swings.

A second consequence of POF is the loss of fertility. Even though some women will spontaneously ovulate and achieve a natural pregnancy most women with POF will not. Infertility treatment is difficult, as in many cases the ovary does not have any follicles left. In the cases where follicles can be detected by biopsy, the ovary has become unresponsive to FSH. Therefore, most women with POF can either choose to adopt children or undergo donor egg IVF. However, obtaining donor eggs can be difficult and the procedure can be very expensive.

The longterm consequences of POF are caused by the increased length of time the body will be without ovarian oestrogen. The risk of osteoporosis and cardiovascular diseases increases after menopause due to a decrease in oestrogen that appears to provide a protective effect against these diseases. Women with POF have reduced oestrogen levels for between 20 to 30 years longer than normal women. Therefore, the risk of these diseases is thought to be much greater in women with POF. For this reason patients with POF are prescribed hormone replacement therapy (HRT). However, these women have an additional concern. The prolonged use of HRT has been associated with an increase in the risk of acqguing breast cancer, endometrial cancer and gallstones. Until research into the long-term effects of HRT in women with POF have been conducted this issue will still be a major concern for these women.

The identification of genes predisposing to POF is therefore an essential step towards understanding the molecular events underlying this condition. It is also critical for clinical management of affected individuals and POF therapy.

Most women with POF are found to have follicles, but they do not appear to respond to normal gonadotrophin stimulation. However, very few mutations have been identified in gonadotrophin hormones or their receptors. The loss of function mutation, 566C>T, identified in the FSH receptor (Aittomaki et al, (1995)) was found to cause ovarian failure with primary amenorrhoea in a group of Finnish families. It appears that this FSH receptor mutation is rare elsewhere, as it has not been detected in other populations (Conway (1997), Layman et al (1998)). Ovarian resistance has also been seen in association with a premature stop codon in the luteinising hormone receptor gene (Latronico et al (1996)). However, while these data demonstrate the obvious importance of the FSH axis in ovarian function, they do not identify which molecular events are causative of POF.

The applicants have now identified a gene in individuals which, when mutated, appears associated with a predisposition on the part of that individual towards POF. It is this finding, and the implications it has for POF screening and management (particularly for individuals with a family history of POF) which underlies the present invention.

SUMMARY OF THE INVENTION

Accordingly, in a first aspect, the invention broadly provides a method of testing to detect whether an individual has, or is predisposed to, POF which comprises the step of detecting the presence or absence of an alteration (mutation) in the gene encoding inhibit.

As used herein, the term "gene encoding inhibin" means INHα, INHβA, and INHβB, together with their non-coding fanling sequences and regulatory elements.

In one (preferred) embodiment, the presence or absence of the mutation is detected through analysis of the DNA encoding inhibin and/or its regulatory elements.

In an alternative embodiment, the presence or absence of the mutation is detected through analysis of mRNA transcribed from the DNA encoding inhibin.

In still a further embodiment, the presence or absence of the mutation is detected through analysis of the amino acid sequence of the expressed inhibin protein.

As a separate embodiment, the invention provides a method of prophylaxis and/or therapeutic treatment against POF of an individual identified as having a risk of POF by a method defined above or suspected to have such a risk which comprises the step of increasing, maintaining and/or restoring the active concentration of wild-type inhibin protein within said individual.

Conveniently, the method will be a gene therapy method and will involve supplying the individual with wild-type inhibin gene function.

Most preferably, the method will involve administering wild-type inhibin to the individual.

In still a further aspect, the invention provides for the use of inhibin in the manufacture of a medicament for treating or preventing POF.

DESCRIPTION OF THE DRAWINGS

While the invention is broadly as defined above, it will be appreciated that it is not limited thereto and that it also includes embodiments of which the following description provides examples. Moreover, a better understanding of the invention will be gained by reference to the accompanying drawings in which:

FIG. 1a shows the results of SSCP of INHβA1 fragments on an 8% polyacrylamide gel containing 5% glycerol. Lane 1 shows a Marker, Lane 2 is non-denatured PCR fragment, Lane 3 is a normal control sample, Lanes 4–11 represent patient samples (patients 1–8, respectively). The extra band in lane 11 (patient 8) indicates a sequence variation.

FIG. 3 shows the results of RFLP analysis of the INHα1 fragment using Bst71I. Undigested DNA gives a single band at 244 bp. Wild-type (W) yields three bands of 134 bp, 85 bp and 25 bp. Homozygosity for the variant yields two ferments of 150 bp and 85 bp. A heterozygote carrier will have all four fragments (150 bp, 134 bp, 85 bp and 25 bp). The variant is heterozygous as it yields both the wild type and variant fragments when digested. The 25 bp fragment is undetectable on this 8% polyacrylamide gel. Lane 1 is a marker lane, lane 2 is undigested DNA, lanes 3–5 represent POF patients identified by DNA sequencing to be heterozygous for the variant, lane 6 is a normal control sample, and lane 7–9 are POF patients shown by DNA sequencing to be homozygous normal for the variant.

FIG. 5 shows age at menopause. The age at menopause was obtained from each patient, and plotted according to age. The three women carrying the 769G>A variant are shown as circles.

DESCRIPTION OF THE INVENTION

As defined above, the method of the invention detects a predisposition to POF or is diagnostic of POF. The critical finding made by the applicants is that at least some instances of POF are due to an alteration (mutation) in the gene encoding inhibin. This finding forms the basis of the present invention.

Inhibin is structurally related to the TGF-β superfamily. The mature inhibin is a 31–32 kDa heterodimeric glyoprotein consisting of an 18 kDa α-subunit linked by two disulphide bonds to one of two 14 kDa β-subunits (Halvorson and Decherney 1996). Therefore there are two forms of inhibin: inhibin A (α-$β_A$), and inhibin B (α-$β_B$). The homodimer of the β-subunit form the glycoprotein activin, which has an opposing function to inhibin. The inhibin subunits are encoded by three separate genes: INHα, INHβA, and INHβB.

As indicated above, INHα, INHβA, and INHβB, together with their non-coding flanking sequences and regulatory elements are collectively referred to herein as the "gene encoding inhibin".

Serum inhibin levels vary across the menstrual cycle and across each of the reproductive stages of life, suggesting that it is an important modulator of the pituitary-gonadal axis and gonadal function (Halvorson and Dechemey 1996). Inhibin increases with the onset of puberty when ovarian function begins, shows cyclic function in the reproductive ovary, and decreases approaching menopause when the ovary enters the non-reproductive state.

The main function of inhibin in the female is the regulation of pituitary FSH secretion. Granulosa cells in both the developing follicle and the corpus luteum secrete inhibin in response to gonadotrophins and other factors such as IGF-1, TGF-β and activin. FSH-induced secretion is in turn suppressed by EGF, TGF-β, and follistatin. Follistatin is an inhibin-like FSH suppressor which also acts as a binding protein for both inhibin and activin regulating their paracrine and autocrine functions (Halvorson and Dechemey 1996).

Developing follicles appear to secrete inhibin B to suppress FSH secretion in the follicular phase. In the luteal phase the sole dimer secreted to regulate FSH is inhibin A. Inhibin along with it's regulation of FSH displays both autocrine and paracrine effects within the ovary. These include the regulation of steroidogenesis, cell growth, and cell differentiation. Inhibin increases androgen production by increasing theca cell responsiveness to LH. It has also been suggested that inhibin along with activin may be involved in a mechanism to select the dominant follicle and to prevent premature luteinisation (Wallace and Healy 1996).

However, to date, there has been no suggestion that an alteration/mutation in the gene encoding inhibin is in any way predictive of susceptibility to POF or is diagnostic of POF.

The amino acid and cDNA nucleotide sequences encoding inhibin are accessible from Genbank. Any change in either sequence is included in the scope of the term "alteration" as used herein.

In terms of inhibin non-coding flanking sequences and regulatory elements, alterations in these may cause transcript instability and/or transcriptional repression. Relevant regulatory regions include the sites for transcript splicing.

In one approach according to the present invention, alteration of the wild-type inhibin gene is detected.

"Alteration of a wild-type inhibin gene" encompasses all forms of alterations including deletions, insertions, missense and point mutations in the coding and noncoding regions. Deletions may be of the entire gene or only a portion of the gene.

Point mutations may result in stop codons, frameshift mutations or amino acid substitutions.

Mutations leading to non-functional gene products are believed to primarily lead to POF. However, mutations which lead to decreased expression of the inhibin gene product may also lead to POF. Point mutation events may occur in regulatory regions, such as in the promoter of the gene, leading to loss or diminution of expresson of the mRNA. Point mutations may also abolish proper RNA processing, leading to loss of expression of the inhibin gene product, or a decrease in mRNA stability or translation efficiency.

A preliminary analysis to detect deletions in DNA sequences can be performed by looking at a series of Southern blots of DNA cut with one or more restriction enzymes, preferably a large number of restriction enzymes. Each blot contains DNA from a series of normal individuals and from a series of test cases. Southern blots displaying hybridizing fragments (differing in length from control DNA when probed with sequences near or including the inhibin locus) indicate a possible mutation. If restriction enzymes which produce very large restriction fragments are used, then pulsed field gel electrophoresis ("PFGE") can be employed.

Detection of point mutations may be accomplished by molecular cloning of the inhibin gene and sequencing that gene using techniques well known in the art. Alternatively, the gene sequences can be amplified, using known polynucleotide amplification techniques, directly from a genomic DNA preparation from the sample tissue. The amplification techniques which can be used include methods such as the polymerase chain reaction (PCR), ligation amplification (or ligase chain reaction, LCR) and amplification methods based on the use of Q-beta replicase. These methods are well known and widely practised in the art. See, eg., U.S. Pat. Nos. 4,683,195 and 4,683,202 and Innis et al., 1990 (for PCR); and Wu et at., 1989a (for LCR). Reagents and hardware for conducting amplification are commercially available. Primers useful to amplify sequences from the inhibin region are preferably complementary to, and hybridize specifically to sequences in the inhibin region or in regions that flank a target region therein.

Inhibin sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

There are numerous well known methods for confirming the presence of a mutant gene. These include: 1) single stranded conformation polymorphism ("SSCP") (Orita et al., 1989); 2) denaturing gradient gel electrophoresis ("DGGE") (Wartell et al., 1990; Sheffield et al., 1989); 3) RNase protection assays (Finkelstein et al., 1990; Kinsler et al., 1991); 4) allele-specific oligonucleotides (ASO's) (Conner et al., 1983); 5) the use of proteins which recognize nucleotide mismatches, such as the E. coli mutS protein (Modrich, 1991); and 6) alle-specific PCR (Rano & Kidd, 1989). For allele-specific PCR, primers are used which hybridize at their 3' ends to a particular inhibin mutation. If the particular inhibin mutation is not present, an amplification product is not observed.

Other approaches which can also be used include the Amplification Refractory Mutation System (ARMS), as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to detect alteration of an allele or an insertion in a polymorphic fragment. Such a method is particularly useful for screening relatives of an affected individual for the presence of the inhibin mutation found in that individual.

In the first three methods (ie., SSCP, DGGE and RNase protection assay), a new electrophoretic band appears. SSCP detects a band which migrates differentially because the sequence change causes a difference in single-strand, intramolecular base pairing. DGGE detects differences in migration rates of mutant sequences compared to wild-type sequences, using a denaturing gradient gel. RNase protection involves cleavage of the mutant polynucleotide into two or more smaller fragments. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches are hybridized nucleic acid duplexes in which the two strands are not 100% complementary. Lack of total homology may be due to deletions, insertions, inversions or substitutions. Mismatch detection can be used to detect point mutations in the gene or its MRNA product. While these techniques are less sensitive than sequencing, they are simpler to perform on a large number of samples.

An example of a mismatch cleavage technique is the RNase protection method. This method involves the use of a labeled riboprobe which is complementary to the human wild-type inhibin gene coding sequence. The riboprobe and either mRNA or DNA isolated from the test tissue are armealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA.

The riboprobe need not be the full length of the inhibin mRNA or gene but can be a segment of either. If the riboprobe comprises only a segment of the inhibin mRNA or gene, it will be desirable to use a number of these probes to screen the whole mRNA sequence for mismatches.

In similar fashion, DNA probes can be used to detect mismatches, through enzymatic or chemical cleavage. See, eg., Cotton et al., 1989; Shenk et al., 1975; Novack et al.,, 1986. Alternatively, mismatches can be detected by shifts in the electrophoretic mobility of mismatched duplexes relative to matched duplexes. See eg. Cariello, 1988. With either riboprobes or DNA probes, the cellular mRNA or DNA which might contain a mutation can be amplified using PCR before hybridization. Changes in DNA of the inhibin gene can also be detected using Southern hybridization, especially if the changes are gross rearrangements, such as deletions and insertions.

DNA sequences of the inhibin gene which have been amplified by use of PCR may also be screened using allele-specific probes. These probes are nucleic acid oligomers, each of which contains a region of the inhibin gene sequence harboring a known mutation. For example, one oligomer may be about 20 nucleotides in length, corresponding to a portion of the inhibin gene sequence. By use of a battery of such allele-specific probes, PCR amplification products can be screened to identify the presence of a previously identified mutation in the inhibin gene.

Hybridization of allele-specific probes with amplified inhibin sequences can be performed, for example, on a nylon filter such as Hybond. Hybridization to a particular probe under stringent hybridization conditions indicates the presence of the same mutation in the sample as in the allele-specific probe.

Mutations from potentially susceptible patients falling outside the coding region of inhibin can be detected by examining the non-coding regions, such as introns and regulatory sequences near or within the inhibin gene. An early indication that mutations in noncoding regions are important may come from Northern blot experiments that reveal messenger RNA molecules of abnormal size or abundance in POF patients as compared to control individuals.

Alteration of inhibin mRNA expression can be detected by any techniques known in the art. These include Northern blot analysis, PCR amplification and RNase protection. Diminished mRNA expression indicates an alteration of the wild-type inhibin gene. Alteration of wild-type mhibin genes can also be detected by screening for alteration of wild-type inhibin protein. For example, monoclonal antibodies immunoreactive with wild-type inhibin can be used to screen a tissue with lack of bound antigen indicating an inhibin mutation.

Monoclonal antibodies with affinities of $10^{-8}$ $M^{-1}$ or preferably $10^{-9}$ to $10^{-10}$ $M^{-1}$ or stronger will typically be made by standard procedures as described, eg. in Harlow & Lane, 1988 or Goding, 1986. Briefly, appropriate animals will be selected and the desired immunization protocol followed. After the appropriate period of time, the spleens of such animals are excised and individual spleen cells fused, typically, to immortalised myeloma cells under appropriate selection conditions. Thereafter, the cells are clonally separated and the supernatants of each clone tested for their production of an appropriate antibody specific for the desired region of the antigen.

Other suitable techniques for preparing antibodies involve in vitro exposure of lymphocytes to the antigenic polypeptides, or alternatively, to selection of libraries of antibodies in phage or similar vectors. See Huse et al., 1989.

Also, recombinant inmunoglobulins may be produced using procedures known in the art (see, for example, U.S. Pat. 4,816,567).

The antibodies may be used with or without modification. Frequently, antibodies will be labeled by joining, either covalently or non-covalently, a substance which provides for a detectable signal. A wide variety of labels and conjugation techniques are known and are reported extensively in the literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241.

Antibodies specific for products of mutant alleles could also be used to detect mutant inhibin gene product. Such antibodies can be produced in equivalent fashion to the antibodies for wild-type inhibin as described above.

The immunological assay in which the antibodies are employed can involve any convenient format known in the art. Such formats include Western blots, immunohistochemical assays and ELISA assays. In addition, functional assays such as protein binding determinations, can also be used.

In summary, any approach to detecting an alteration in the underlying DNA coding for wild-type inhibin expression can be employed, whether the nalysis be of the DNA itself, mRNA transcribed from the DNA or the protein which is the ultimate expression product of the DNA.

The following experimental sections outline various analyses undertaken in detail. These are included for reasons of exemplification only.

Experimental

Materials and Methods

DNA Extraction

Genomic DNA was extracted from 10 ml samples of blood. Lymphocytes were isolated from blood samples using the NYCOMED LymphoprepTM Kit. Cells were incubated at 65° C. for 1 hour with 3.5 ml 6 M GuHCl2, 250 μl 7.5 M NH4Ac, 50 μl 10 mgml-1 Proteinase K and 250 μl 20% Na Sarcosyl. Cells were added to 2 ml of cold CHCL3 and then spun at 2000 rpm for 3 minutes. The top laver was collected and added to 10 ml of cold absolute ethanol to precipitate the DNA. DNA was stored in 200 μl TE buffer at 4° C.

Normal DNA samples, required for examining the prevalence of a variant in the general population, were obtained from the saliva of volunteers (method adapted from the Promega Wizard Genomic DNA Purifcation Kit). Saliva samples were collected from subjects 10 minutes after rinsing their mouth with water to remove any food deposits. Samples were stored at 4° C. until DNA extraction could be performed. 1 ml of saliva was added to 4 ml of phosphate-buffered saline (PBS), pH 7.1, and centrifuged at 3000 rpm for 5 minutes. The pellet was resuspended in 180 μl of PBS and 20 μl of 20 mg/ml RNAse A solution. Cells were with 300 μof Nuclear Lysis Solution (Promega Kit) and protein was then precipitated by vortexing with 100 ml of Protein Precipitation Solution (Promega Kit), followed by centrifugation at 13000 rpm for 3 minutes. The supernatant was collected and DNA precipitated with 300 μl of isopropanol and centrifugation for one minute at 13000 rpm. The DNA pellet was resuspended in 100 μl of DNA Hydration Solution (Promega Kit) and stored at 4° C.

Polymerase Chain Retion (PCR)

PCR primers were designed spanning the functional subunit of each gene for INHα (Mayo et al (1986)), INHβA (Mason et al (1986)), and INHβB (Mason et al (1986)) using the Primer Select module in the DNAStar computer programme from Lasergene, 1994. Primers flanking the whole region were designed to give one large fragment for each gene, which was used for DNA sequencing. Smaller overlapping fragments of 200–300 bp were designed that spanned the functional region and were used for SSCP analysis. The primers flanking each fragment are shown in Table 1.

TABLE 1

| Fragment | Size | PRIMERS (5' TO 3') | LOCATION |
|---|---|---|---|
| Inhibin Alpha | | | |
| INHα | 601 bp | For GCTGCTGCGCTGTCCCCTCTGTA (SEQ ID NO: 10) Rev TATTTCCCAACTCTGCCTTTCCTC (SEQ ID NO: 11) | 732 . . . 754 1332 . . . 1309 |
| INHα1 | 243 bp | For GGCCCACACTCGGACCAGAC (SEQ ID NO: 12) Rev AGCCCACAACCACCATGACAGTAG (SEQ ID NO: 13) | 792 . . . 811 1034 . . . 1011 |
| INHα2 | 139 bp | For GCTGGGCTGGGAACGGTGGAT (SEQ ID NO: 14) Rev GGAGTAGGGCTGGGCTGGGGTAGG (SEQ ID NO: 15) | 963 . . . 983 1101 . . . 1078 |
| INHα3 | 254 bp | For CTACCCCAGCCCAGCCCTACTCCT (SEQ ID NO: 16) Rev TATTTCCCCAACTCTGCCTTTCCTG (SEQ ID NO: 17) | 1079 . . . 1102 1332 . . . 1309 |

TABLE 1-continued

| Fragment | Size | PRIMERS (5' TO 3') | LOCATION |
|---|---|---|---|
| Inhibin Beta A | | | |
| INHβA | 529 bp | For CTGGGCAAGAAGAAGAAGAAAGAA (SEQ ID NO: 18) Rev CCTGGGCTGGGCAACTC (SEQ ID NO: 19) | 1005 . . . 1028 1533 . . . 1517 |
| INHβA1 | 302 bp | For GCAGGAGCAGATGAGGAAAAGGGAG (SEQ ID NO: 20) Rev CGCATGCGGTAGTGGTTGAT (SEQ ID NO: 21) | 1017 . . . 1094 1372 . . . 1253 |
| INHβA2 | 268 bp | For GGCACGTCCGGGTCCTCACTG (SEQ ID NO: 22) Rev TCTTCATTTTGCCACTGTCTTCTC (SEQ ID NO: 23) | 1314 . . . 1334 1581 . . . 1558 |
| Inhibin Beta B | | | |
| INHβB | 586 bp | For CGTGGTGCCGGTGTTCGTGGAC (SEQ ID NO: 24) Ref CTCCACAGCCCAACAGAATGACT (SEQ ID NO: 25) | 617 . . . 638 1185 . . . 1163 |
| INHβB1 | 202 bp | For CGTGGTGCCGGTGTTCGTGGAC (SEQ ID NO: 26) Rev GCCGCTGGGTGCTATGAT (SEQ ID NO: 27) | 617 . . . 638 1185 . . . 1163 |
| INHβB2 | 218 bp | For GCACCCACCGGCTACTACG (SEQ ID NO: 28) Rev TCCCGCTTGACGATGTTGT (SEQ ID NO: 29) | 807 . . . 825 1024 . . . 1006 |
| INHβB3 | 241 bp | For AACTCCTGCTGCATTCCCACCAA (SEQ ID NO: 30) Rev CTCCACAGCCCAACAGAATGACT (SEQ ID NO: 31) | 945 . . . 967 1185 . . . 1163 |

The primers were dissolved in sterile water to give a final concentration of 20 mM.

PCR Conditions

PCR was carried out using Qiagen Taq DNA polymerase and PCR buffer. Genomic DNA (100 ng) was amplified in a 25 μl volume reaction containing 2.5 μl of PCR buffer (1×), 25 nmol of each dNTP, 5 nmol of forward and reverse primers, and 0.125 μl Taq DNA polymerase. β-globin was used as positive control and a nill DNA reaction was used as a negative control for all PCR reactions. Standard PCR conditions comprised 94° C. denaturation for 1 minute, 58° C. annealing for 1 minute and 72° C. extension for 1 minute for 30 cycles. Touchdown PCR conditions comprised 20 cycles of denaturation at 94° C. for 45 seconds, annealing at 65° C. –55° C (–0.5° C. /cycle) for 45 seconds and extension at 72° C. for 1 minute, followed by 15 additional cycles with annealing at 55° C. All four inhibin α fragments INHα (601 bp), INHα1, INHα2, and INHα3, along with the large inhibin βA fragment, INHβA (529 bp), and large inhibin βB fragment, INHβB (586 bp), were amplified using touchdown PCR and 5 μl of Qiagen Q solution per reaction. The two smaller inhibin βA fragments (INHβA1, INHβA2) and three smaller inhibin βB fragments (INHβB1, INHβB2, INHβB3, were amplified under standard PCR conditions.

To ensure that a single band of expected size was present after amplification, electrophoresis of 5 μl of each PCR product was carried out in a 1.5% agarose gel and visualised under UV light using an ethidium bromide stain.

Single Stranded Conformation Polymorphism (SSCP)

An initial group of samples from 12 patients were analysed by SSCP analysis, to determine whether this was a suitable mutation detection strategy. The remaining 32 samples were all analysed by DNA sequencing only. The PCR products were diluted ¹/₁₀ with sterile water. Equal volumes of diluted sample and 2× formamide loading buffer were heated to 95° C. for 3 minutes to denature the samples, and immediately placed on ice to prevent DNA strands from reannealing. A 3 μl aliquot of each sample were electrophoresed alongside non-denatured and denatured controls. The SSCP gels consisted of 1× TBE buffer, 8% or 10% polyacrylamide, with or without glycerol (5%). Setting agents were 15 μl 25% (w/v) ammonium persulphate and 15 μl TEMED for every 10 ml of non-denatuing gel. Electrcophoresis was performed at room temperature (20–24° C.) using 0.5×TBE running buffer. Mini gels (BioRad miniprotean II cell) were electrophoresed for 2–3 hours at: 170 V and large gels (BioRad SequiGen Sequencing cell) where electrophoresed overnight at 200–300 V. The DNA was visualised using silver staining. Gels were fixed in equal volumes of 40% ethanol and 10% acetic acid for a least 30 minutes, followed by two 15-minute washes in a second mixture of 10% ethanol and 5% acetic acid. Fixation was followed by a 15-minute wash in a K2Cr2O7 based oxidiser. Gels were then washed in distilled water until yellow coloration of the oxidiser was completely removed. The gels were then stained in 20 mls of silver reagent dissolved in 180 ml of distilled water for 20 minutes. Development of the gels was performed by washing in distilled water for one minute followed by three washes in 200 ml aliquots of developer, and a final 5-minute wash in 5% acetic acid. The gels were washed to remove the acetic acid, transferred to Whatman 3 mm filter paper, dried and stored.

DNA Sequencing

The large PCR fragments, INHα(601 bp), INHβA (529 bp) and INHβB (586 bp), that spanned the entire functional region of each of the three inhibin genes, were used as templates for DNA sequencing. Samples were purified with Promega's Wizard PCR Preparations DNA Purification System and sequencing was performed using an Applied Biosystems Model 377 automated sequencer and 2 μl of template DNA.

Characterisation of Variants

Figure 1A:
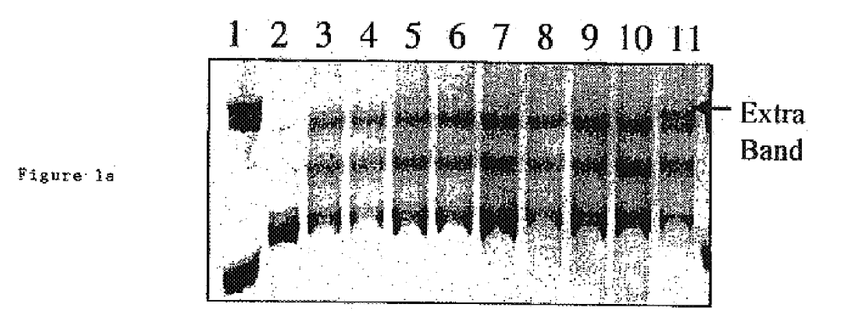
Figure 1B:
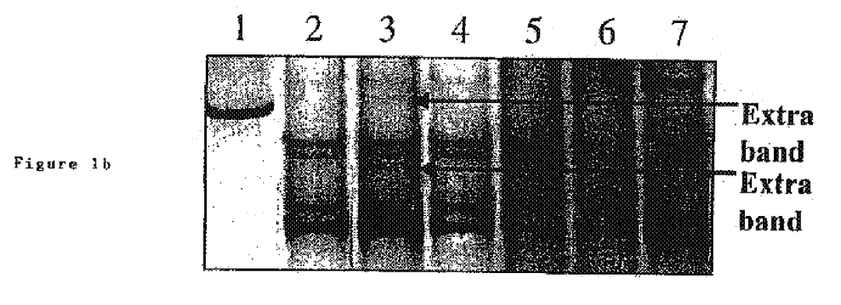
FIG. 1b shows the results of SSCP of INHβ1 fragments on an 8% polyacrylamide gel Lane 1 shows a Marker, Lane 2 is a normal control sample, Lanes 3–7 represent patient samples (patients 1–5, respectively). The extra band in lane 3 (patient 1) indicates a sequence variation.

The PCR products from a sample of the population were analysed for the variant 769G>A in the INHα gene subunit. RFLP analysis used Bst71I as the restriction enzyme to determine if this varant was a naturally occurnng polymorphism or a mutation that may be responsible for POF. Normal DNA was collected from saliva samples of fifty men and women of any age as a representation of the general population. DNA with a known sequence was used as negative control DNA, while DNA from patient 1 (Lane 3, FIG. 1b) shown to be a carrier of the variant 769G>A acted as a positive control for the variant. The restriction enzyme digest was undertaken in 1×restriction buffer using 2.5 U of Bst71I, 0.2 μl of acetylated BSA, 5 μl of PCR product, and sterile water to give a total reaction volume of 20 μl. The reaction mixoes were incubated at 37° C. for 1–2 hours, electrophoresed in a 2% agarose gel and stained with ethidium bromide. To allow better separation of the fragments, some of the samples were also electrophoresed in an 8% polyacrylmide gel and subsequently stained with Sybr Gold. The undigested DNA control was also incubated in a reaction mixture containig all the above reagents except the Bst71I enzyme, and electrophoresed along side the digested PCR products. The wildtype INHα1 PCR product yields three fragments of 85 bp, 25 bp and 134 bp when digested with Bst71I. In the presence of the 769G>A variant, the enrne recognition site CGTCG(n)12 is abolished and hence yields only two fragments of 85 bp and 159 bp. A heterozygous sample will display all four fragments.

Results

Two variants were detected using SSCP analysis in an initial group of 12 unrelated New Zealand POF patients. First, a variant was seen in the INHβA1 fragmnent of patient 8 (Lane 11, FIG. 1a). Second, the INHα1 fragment displayed extra bands in patient 1 compared with wildtype DNA (Lane 3, FIG. 1b). The fragments INHα2, INHα3, INHβA2, INHβA1, INHβB1, INHβB2, and INHβB3 did not reveal any migration variants in any of the patient samples when compared against the wildtype DNA (data not shown).

Figure 2A:
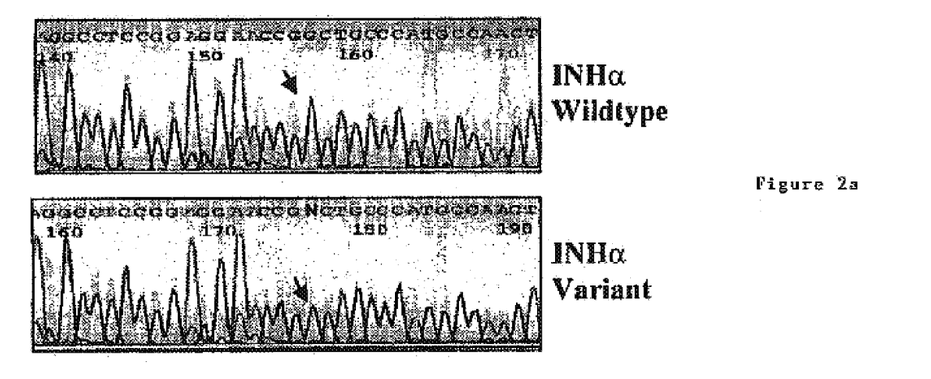
FIG. 2a is an Electropherogram displaying the sequence of the INHβA1 variant (patient 8) compared to the wild-type (WT) sequence. Arrows indicates C to T sequence change in the variant, and the corresponding nucleotide in the wild-type sequence.

The migrational shift detected inm the INHβA1 fragment was caused by a silent substitution at nucleotide 1032C>T (FIG. 2a). This variant did not change the amino acid sequence of inhibin beta A subunit as it occurred in the third position of the codon, causing a GGC (glycine) to GGT (glycine) alteration.

Figure 2B:
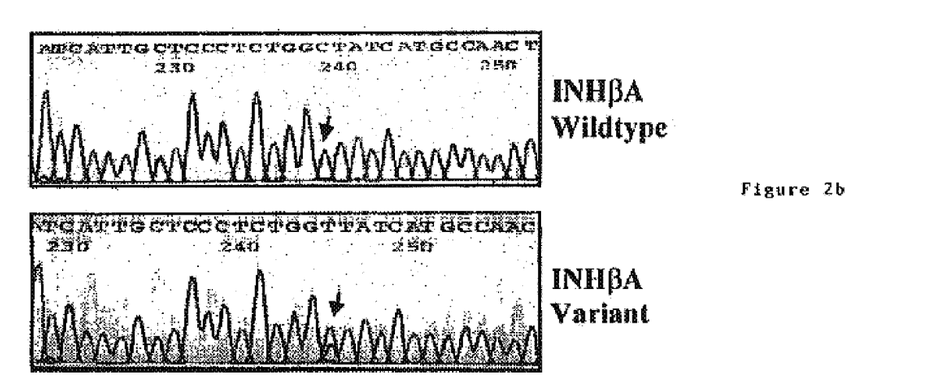
FIG. 2b is an Electropherogram displaying the sequence of the INHα1 variant (patient 1) compared to the wild-type (WT) sequence. Arrows indicates G to A sequence change in the variant, and the corresponding nucleotide in wild-type sequence.
Figure 3:
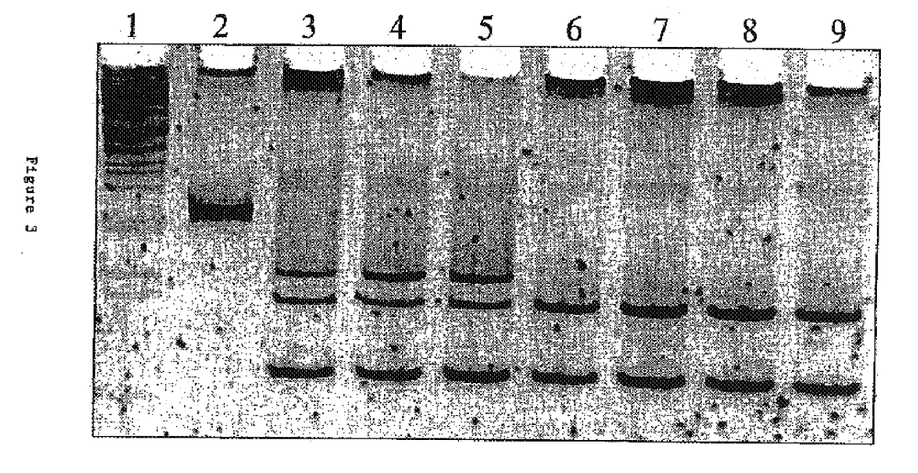
Figure 4:
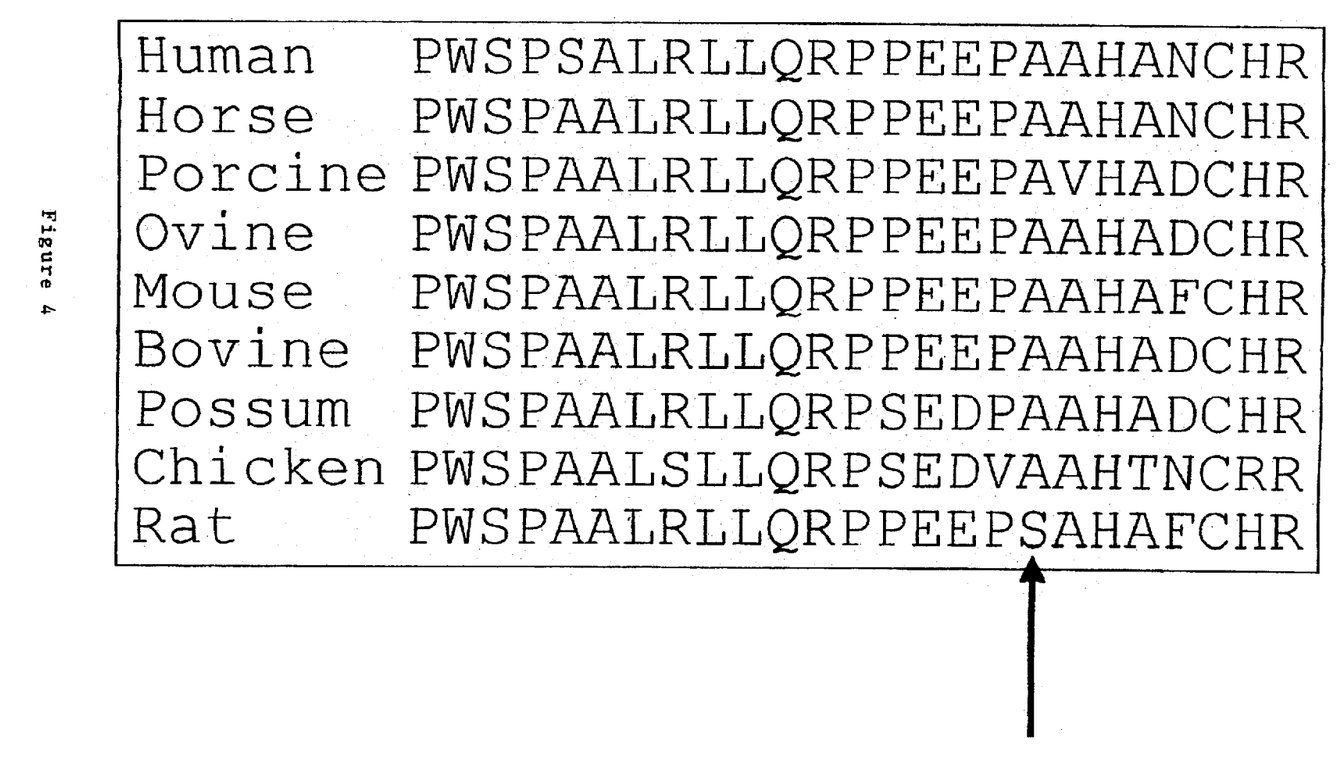
FIG. 4 shows the alignment of the INHα gene subunit amino acid sequences from the human, horse, porcine, ovine, mouse, bovine, possum, chicken and rat. DNA sequences were obtained from Genbank. The arrow indicates the amino acid altered by the G>A mutation.
Figure 5:
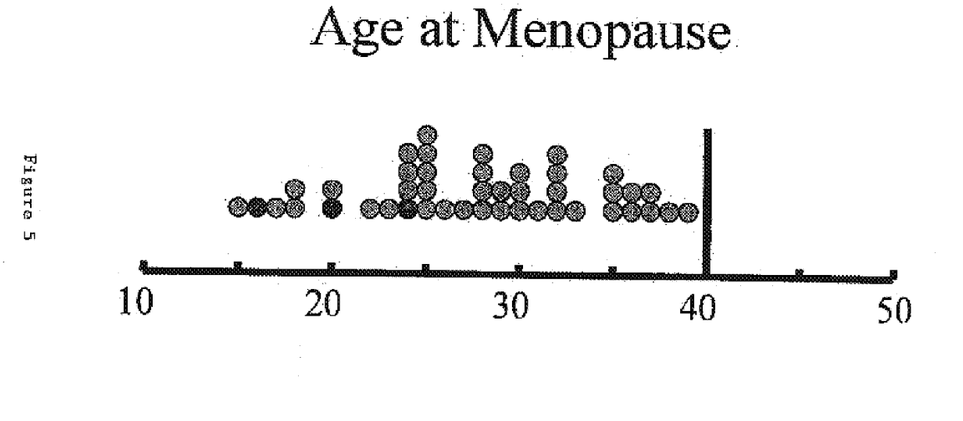

Direct DNA sequencing of the PCR product confirmed the INHα1 variant detected using SSCP. The variant was the result of a G>A missense substitution at nucleotide 769 (FIG. 2b) that alters codon 257 from GCT to ACT, resulting in an alanine to threonine sammo acid substitution in the INHA gene subunit. To confirm that the INHα769G>A variant was not a sequencing error, the INHα1 fragment was amplified from both the original DNA sample, DNA extracted from a second blood sample, and each was sequenced in both directions. Again the same sequence variation was identified. Finally, sequencing was performed on the INHα amplification products of all 12 patients and no additional variants were found.

DNA was collected fiom a further six affected women with POF from New Zealand, one from Finland and 25 from Slovenia. DNA was also collected from seven women with primary amenorrhoea. The fragments INHα (601 bp), INHβA (529 bp), and INHβB (586 bp) were amplified from all 44 apparently unrelated POF patients and 7 primary amenorrhoea patients. Another two patients were found to carry the INHα 769G>A variant.

A rapid RFLP screen was developed to identify the presence of the INHα 769G>A variant. This vanant abolished a Bst71I restriction enzyme site. An RFLP analysis of the 244 bp INHα amplification products from DNA samples of 48 normal individuals showed only 134 bp and 85 bp fragments; the smallest 25 bp fragment was not visible (data not showm). The patient with the 769G>A variant demonstrated heterozygosity with fragment lengths of 159 bp, and 134 bp and 85 bp.

Discussion

The INHα 769G>A transition resulted in an alanine to threonine substitution at codon 196. RFLP analysis revealed that this variant is rare in the normal population. It is likely to be a non-conservative substitution as the alanine to threonine results in the addition of an aliphatic hydroxyl group in the side chain of the functional group.

The hydroxyl group results in threonine being more hydrophilic and reactive than alanine.

The human inhibin alpha gene demonstrates 80% homology with equine, bovine, porcine, ovine, rat and mouse sequences (Yamanouchi, Yoshida et al. 1995). The amino acid alanine was conserved at the site of the mutation in all of these sequences, with exception to the rat sequence. The rat sequence contained a serine instead of an alanine. Serine is the hydroxylated version of alanie Threonine, however, has the addition of a methyl group as well as the hydroxyl group making it a large amino acid. Therefore, the substitution of anine for serine in the rat is a more conservative alteration than the threonine substitution induced by the INHα mutation. Also, the rat is most divergent when compared with the human INHα gene of all these species.

Inhibin alpha shows amino acid sequence homology to TGF-β2 transforming growth factor-β2) and OP-1 (oestrogenic protein-1) of 24% and 26%, respectively Kinsley, 1994). The 3-dimensional crystal structure of TGF-β2 and OP-1 is known, and all three appear to show a characteristic 7-cystein domain resulting in a ring structure named the cysteine knot. The 769G>A transition is adjacent to the first cysteine residue that foims a disulphide bond with the fifth cysteine residue. Consequently, the mutation is drawn into close proximity with the fourth cysteine residue, which forms the disulphide bond involved in dimerisation. Therefore, this mutation has the potential to disrupt the binding of the inhibin alpha subunit to the inhibin beta subunit. This may be directly, by disrupting the disulphide bond involved in dimmer formation, or indirectly, by disrupting the tertiary structure of the cysteine knot and therefore inhibiting its ability to dimerise.

Industrial Application

The demonstration that mutations in inhibin genes (particularly INHα) are associated with instances of POF has a number of implications. As indicated above, the primary implication is in a method of detection of a risk of a predisposition to POF or a method of POF diagnosis.

Early at-risk determination provides the opportunity for early intervention. Carriers of the mutation could choose to have treatment prior to the emergence of any problem. Testing also enables carriers to make important life decisions (eg. early child bearing). For non-carriers, in a family with a history of POF testing will bring peace of mind and will remove the need for surveillance.

The identification of inhibin as a putative POF susceptibility gene has implications beyond early detection. The possibility of preventative approaches to delay the onset of POF is also raised.

These involve, primarily the direct adminstration to the susceptible female of wild-type inhibin in a sufficient amount to restore the active concentration of inhibin to putatively "normal" levels.

For such an approach, the inhibin can be prepared as a medicament, in combination with conventional carers, vehicles, diluents or excipients.

There is also the possibility of a curative or corrective approach using gene therapy. This willl involve supplying wild-type inhibin function to an individual who carries mutant inhibin genes. Supplying such a function should prevent POF developing. The wild-type inhibin gene or a part of the gene may be introduced into cells within such an individual in a vector such that the gene remains extrachromosomal. In such a situation, the gene will be expressed by the cell from the extrachromosomal location. More usual is the situation where the wild-type inhibin gene or a part thereof is introduced into the mutant cell in such a way that it integrates into the genomic DNA. Less usual is the situation where the wild-type inhibin gene or a part thereof is introduced into the mutant cell in such a way that it recombines with the endogenous mutant inhibin gene present in the cell. Such recombination requires a double recombination event which results in the correction of the inhibin gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art.

As generally discussed above, the wild-type inhibin gene or fagment, where applicable, may be employed in gene therapy methods in order to increase the amount of the expression products of such genes in target cells. Such gene therapy is partcularly appropriate for use in cells in which the level of inhibin polypeptide is absent or diminished compared to normal cells. It may also be useful to increase the level of expression of a given inhibin gene even in those cells in which the mutant gene is expressed at a "normal" level, but the gene product is not fully functional.

Gene therapy would be carried out according to generally accepted methods, for example as described by Kren et al., (1998), or as described by Friedman in *Therapy for Genetic Disease,* T. Friedman, ed., Oxford University Press (1991), pp 105–121. Cells from a patient would be first analyzed by the methods described above, to ascertain the production of inhibin polypeptide. A virus or plasmid vector, containing a copy of the inhibin gene linked to expression control elements and capable of replicating inside the target cells, is prepared. Suitable vectors are known, such as disclosed in U.S. Pat. No. 5,252,479 and PCT published application WO 93/07282. The vector is then injected into the patient, either locally at the site of the target cells or systemically (in order to reach any target cells that may be at remote sites). If the transfected gene is not permanently incorporated into the genome of each of the targeted cells, the treatment may have to be repeated periodically.

Gene transfer systems known in the art may be useful in the practice of the gene therapy methods. These include viral and nonviral transfer methods. A number of viruses have been used as gene transfer vectors, including papovaviruses (eg. SV40, Madzak et al., (1992)), adenovirus (Berkner (1992)), vaccinia virus (Moss (1992)), adeno-associated virus (Muzyczka (1992)), herpesviruses including HSV and EBV (Margolskee (1992); Johnson et al., (1992); Fink et al., (1992); Breakfield and Geller, (1987); Freese et al., (1990)), and retroviruses of avian (Petropoulos et al., (1992), murine (Miller (1992)); and human, origin (Shimada et al., (1991); Helseth et al., (1990); Page et al., (1990); Buchschacher and Panganiban (1992)).

Nonviral gene transfer methods known in the art include chemical techniques such as calcium phosphate coprecipitation (Pellicer et al, (1980)); mechanical techniques, for example microinjection (Anderson et al., (1980)); membrane fusion-mediated transfer via liposomes (Lim et al, (1992)); and direct DNA uptake and receptor-mediated DNA transfer (Wolff et al., (1990); Wu et al., (1991)). Viral-mediated gene transfer can be combined with direct in muoa gene transfer using liposome delivery, allowing one to direct the vial vectors to the target cells. Alternatively, the retroviral vector producer cell line can be injected into the patient (Culver et al., 1992). Injection of producer cells would then provide a continuous source of vector particles.

In an approach which combines biological and physical gene transfer methods, plasmid DNA of any size is combined with a polylysine-conjugated antibody specific to the adenovirus hexon protein, and the resulting complex is bound to an adenovirus vector. The trimolecuar complex is then used to infect cells. The adenovirus vector permits efficient binding, internalization, and degradation of the endosome before the coupled DNA is damaged.

Liposome/DNA complexes have been shown to be capable of mediating direct in uivo gene transfer. While in standard liposome preparations the gene transfer process is nonspecific, localized in two uptake and expression have been reported in tissue deposits, for example, following direct in situ administration (Nabel, 1992).

Those persons skilled in the art will appreciate that the above description is provided by way of example only and that it is limited only by the lawful scope of the appended claims.

References

Anderson, et al (1980). *Proc. Natl. Acad Sci USA* 77:5399–5403.
Berkner (1992). *Curr. Top. Microbiol. Immunol.* 158:39–61.
Breakfield and Geller (1987). *Mol. Neurobiol.* 1:337–371.
Buchschacher and Panganiban (1992). *J. Virol.* 66;2731–2739.
Cariello (1988). *Human Genetics* 42:726.
Conner, B. J., et al (1983). *Proc. Nat. Acad. Sci USA.* 80:278–282.
Culver, et al. (1992). *Science* 256:1550–1552.
Fink, et al. (1992). *Hum. Gene Ther.* 3:11–19.
Finkelstein, J., et al. (1990). *Genomics* 7:167–172.
Freese, et al. (1990). *Biochem. Pharmacol.* 40:2189–2199.
Goding (1986). *Monoclonal Antibodies: Principles and Practice,* 2d ed. (Academic Press, New York).
Harlow & Lane (1988). *Antibodies: A Laboratory Manual,* (Cold Spring Harbor Laboratory, Cold Spring Harbor, N.Y.).
Helseth et al,. (1990). *J. Virol.* 64:2416–2420.
Huse, et al,. (1989). *Science* 246:1275–1281.
Innis et al., (1990). *PCR Protocols: A Guide to Methods and Applications,* (Academic Press, San Diego).
Johnson, et al., (1992). *J. Virol.* 66:2952–2965.
Kinszler, K. W., et al., (1991). *Science* 251:1366–1370.
Kren et al., (1998). *Nature Medicine,* 4, 285–290.
Lim, et al., (1992). *Circulation* 83:2007–2011.
Madzak, et al., (1992). *J. Gen. Virol.* 73:1533–1536.
Maniatis, T. et al., (1982). *Molecular cloning: A laboratory manual (Cold Spring Harbor Laboratory, Cold Spring Harbor, N.Y.).*
Margolskee (1992). *Curr. Top. Microbial. Immunol.* 158:67–90.
Merrifield (1963). *J. Am. Chem. Soc.* 85:2149–2156.
Modrich, P. (1991). *Ann. Rev. Genet.* 25:229–253.
Moss (1992). *Curr. Top. Microbiol. Immunol.* 158:25–38.
Muzyczka (1992). *Curr. Top. Microbiol. Immunol.* 158:97–123.
Newton, C. R., Graham, A., Heptinstall, L. E., Powell, S. J., Summers, C., Kalsheker, N., Smith, J. C., and Markham, A. F. (1989). *Nucl. Acids Res.* 17:2503–2516.
Novack, et al., (1986). *Proc. Nat. Acad. Sci. USA* 83:586.
Orita, et al., (1989). *Proc. Nat. Acad. Sci. USA* 86:276–2770.
Orita, et al., (1989). *Genomics* 5:874–879.
Page, et al., (1990). *J. Virol.* 64:5370–5276.
Petropoulos, et al., (1992). *J. Virol.* 66:3391–3397.
Rano & Kidd (1989). *Nucl. Acids Res.* 17:8392.
Sambrook, J., et al., (1989) *Molecular cloning: A laboratory manual,* $2^{nd}$ Ed. (Cold Spring Harbor Laboratory, Cold Spring Harbor, N.Y.).
Scharf (1986). *Science* 233:1076.
Sheffield, V. C., et al., (1989). *Proc. Nat. Acad. Sci. USA* 86:232–236.
Shenk, et al., (1975). *Proc. Nat. Acad. Sci. USA* 72:989.
Shimada, et al., (1991). *J. Clin. Invest* 88:1043–1047.

Wartell, R. M., et al., (1990). *Nucl. Acids. Res.* 18:2699–2705.
Wolff, et al., (1990). *Science* 247:1465–1468.
Wu, et al., (1989a). *Genomics* 4:560–569.
Wu, et al., (1991). *J. Biol Chem.* 266:14338–14342.
Aittomaki, K., J. L. Lucena, et al. (1995). *Cell* 82(6): 959–68.
Bione, S., C. Sala, et al. (1998). *American Journal of Human Genetics* 62(3): 533–541.
Buckler, H. M., D. L. Healy, et al. (1993). *Gynecological Endocrinology* 7(2): 123–8.
Burger, H. G., N. Cahir, et al. (1998). *Clinical Endocrinology* 48(6): 809–813.
Conway, G. S., S. Hettiarachchi, et al. (1995). *Lancet* 346(8970): 309–10.
Conway, G. S. (1997). *Current Opinion in Obstetrics & Gynecology* 9(3): 202–206.
Coulam, C. B., S. C. Adamson, et al. (1986). *Obstetrics & Gynecology* 67(4): 604–6.
Devi, A. S., D. A. Metzger, et al. (1998). *Fertility & Sterility* 70(1): 89–93.
Halvorson, L. M. and A. H. c. Dechemey (1996). *Fertility & Sterility* 65(3): 459–469.
Hofmann, G. E., D. R. Danforth, et al. (1998). *Fertility & Sterility* 69(3): 474–477.
Latronico, A. C., Y. Chai, et al. (1998). *Molecular Endocrinology* 12(3): 442–50.
Layman, L. C., M. E. Shelley, et al. (1993). *Fertility & Sterility* 60(5): 852–7.
Liao, W. X., A. C. Roy, et al. (1998). *Fertility & Sterility* 69(1): 102–6.
Mason, A. J., H. D. Niall, et al. (1986). *Biochemical & Biophysical Research Communications* 135(3): 957–64.
Mayo, K. E., G. M. Cerelli, et al. (1986). *Proceedings of the National Academy of Sciences of the United Sates of America* 83(16): 5849–53.
Pampfer, S. and K. Thomas (1989). *Jounal de Gynecologie, Obstetrique et Biologie de la Reproduction* 18(3): 279–87.
Partington, M. W., D. Y. Moore, et al. (1996). *American Journal of Medical Genetics* 64(2): 370–2.
Reame, N. E., T. L. Wyman, et al. (1998). *Journal of Chmiocal Endocrinology & Metabolism* 83(9): 3302–3307.
Roberson, D. M. and D. M. de Kretser (1989). *Molecular & Cellular Endocrinology* 62(2): 307–11.
Sala, C., G. Arrigo, et al. (1997). *Genomics* 40(1): 123–131.
Santoro, N., A. L. Schneyer, et al. (1992). *Obstetrics Gynecology* 79(4): 579–85.
Tierney, M. L., N. H. Goss, et al. (1990). *Endocrinology* 126(6): 3268–70.
Vaughan, J. M. and W. W. Vale (1993). *Endocrinology* 132(5): 2038–50.
Wallace, E. M. and D. L. c. Healy (1996). *British Journal of Obstetrics & Gynaecology* 103(10): 945–956.
Whitney, E. A., L. C. Layman, et al. (1995). *Fertility & Sterility* 64(3): 518–24.
Yamanouchi, K., S. Yoshida, et al. (1995). *Journal of Veterinary Medical Science* 57(5): 905–9.

What is claimed is:

1. A method of testing to detect whether a human female subject is predisposed to Premature Ovarian Failure (POF), the method comprising at least a step of detecting the nucleotide present at position 769 of the gene encoding inhibin alpha in said subject, wherein the presence of an A at said position is indicative of a predisposition to POF.

2. The method of claim 1, wherein said nucleotide is detected by analysis of DNA.

3. The method of claim 1, wherein said nucleotide is detected by analysis of RNA.

4. The method of claim 1, wherein said nucleotide is detected by nucleotide sequencing.

5. The method of claim 1, wherein said nucleotide is detected by Restriction Fragment Length Polymorphism (RFLP) analysis using the restriction enzyme Bst71I.

6. A method of testing to detect whether a human female subject is predisposed to Premature Ovarian Failure (POF), the method comprising at least a step of detecting the amino acid present at position 257 of inhibin alpha, wherein the presence of threonine at said position is indicative of a predisposition to POF.

7. The method of claim 6, wherein said amino acid is detected by amino acid sequencing.

* * * * *

```
                         SEQUENCE LISTING

<160> NUMBER OF SEQ ID NOS: 35

<210> SEQ ID NO 1
<211> LENGTH: 25
<212> TYPE: PRT
<213> ORGANISM: Homo sapiens

<400> SEQUENCE: 1

Pro Trp Ser Pro Ser Ala Leu Arg Leu Leu Gln Arg Pro Pro Glu Glu
 1               5                  10                  15

Pro Ala Ala His Ala Asn Cys His Arg
                20                  25

<210> SEQ ID NO 2
<211> LENGTH: 25
<212> TYPE: PRT
<213> ORGANISM: Equus caballus

<400> SEQUENCE: 2

Pro Trp Ser Pro Ala Ala Leu Arg Leu Leu Gln Arg Pro Pro Glu Glu
 1               5                  10                  15

Pro Ala Ala His Ala Asn Cys His Arg
                20                  25

<210> SEQ ID NO 3
<211> LENGTH: 25
<212> TYPE: PRT
<213> ORGANISM: Sus scrofa

<400> SEQUENCE: 3

Pro Trp Ser Pro Ala Ala Leu Arg Leu Leu Gln Arg Pro Pro Glu Glu
 1               5                  10                  15
```

```
Pro Ala Val His Ala Asp Cys His Arg
            20              25

<210> SEQ ID NO 4
<211> LENGTH: 25
<212> TYPE: PRT
<213> ORGANISM: Ovis aries

<400> SEQUENCE: 4

Pro Trp Ser Pro Ala Ala Leu Arg Leu Leu Gln Arg Pro Pro Glu Glu
  1               5                  10                  15

Pro Ala Ala His Ala Asp Cys His Arg
            20              25

<210> SEQ ID NO 5
<211> LENGTH: 25
<212> TYPE: PRT
<213> ORGANISM: Mus sp.

<400> SEQUENCE: 5

Pro Trp Ser Pro Ala Ala Leu Arg Leu Leu Gln Arg Pro Pro Glu Glu
  1               5                  10                  15

Pro Ala Ala His Ala Phe Cys His Arg
            20              25

<210> SEQ ID NO 6
<211> LENGTH: 25
<212> TYPE: PRT
<213> ORGANISM: Bos sp.

<400> SEQUENCE: 6

Pro Trp Ser Pro Ala Ala Leu Arg Leu Leu Gln Arg Pro Pro Glu Glu
  1               5                  10                  15

Pro Ala Ala His Ala Asp Cys His Arg
            20              25

<210> SEQ ID NO 7
<211> LENGTH: 25
<212> TYPE: PRT
<213> ORGANISM: Didelphis marsupialis

<400> SEQUENCE: 7

Pro Trp Ser Pro Ala Ala Leu Arg Leu Leu Gln Arg Pro Ser Glu Asp
  1               5                  10                  15

Pro Ala Ala His Ala Asp Cys His Arg
            20              25

<210> SEQ ID NO 8
<211> LENGTH: 25
<212> TYPE: PRT
<213> ORGANISM: Gallus sp.

<400> SEQUENCE: 8

Pro Trp Ser Pro Ala Ala Leu Ser Leu Leu Gln Arg Pro Ser Glu Asp
  1               5                  10                  15

Val Ala Ala His Thr Asn Cys Arg Arg
            20              25

<210> SEQ ID NO 9
<211> LENGTH: 25
<212> TYPE: PRT
<213> ORGANISM: Rattus sp.
```

-continued

```
<400> SEQUENCE: 9

Pro Trp Ser Pro Ala Ala Leu Arg Leu Leu Gln Arg Pro Pro Glu Glu
 1               5                  10                  15

Pro Ser Ala His Ala Phe Cys His Arg
            20                  25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
gctgctgcgc tgtcccctct gta                                              23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 11
tatttcccaa ctctgccttt cctc                                             24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
ggcccacact cggaccagac                                                  20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
agcccacaac caccatgaca gtag                                             24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
gctgggctgg gaacggtgga t                                                21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
ggagtagggc tgggctgggg tagg                                             24
```

```
<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16 ctacccagc ccagccctac tcct                                    24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
tatttcccca actctgcctt tcctc                                  25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
ctgggcaaga agaagaagaa agaa                                   24

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 19
cctgggctgg gcaactc                                           17

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 20
gcaggagcag atgaggaaaa gggag                                  25

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
cgcatgcggt agtggttgat                                        20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer
```

```
<400> SEQUENCE: 22
ggcacgtccg ggtcctcact g                                              21

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
tcttcatttt gccactgtct tctc                                           24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 24
cgtggtgccg gtgttcgtgg ac                                             22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 25
ctccacagcc caacagaatg act                                            23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
cgtggtgccg gtgttcgtgg ac                                             22

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 27
gccggtgggt gctatgat                                                  18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 28
gcacccaccg gctactacg                                                 19

<210> SEQ ID NO 29
<211> LENGTH: 19
```

```
<212> TYPE: DNA
<213> ORGANISM: Artificial Sequence
<220> FEATURE:
<223> OTHER INFORMATION: Description of Artificial Sequence: Primer

<400> SEQUENCE: 29
tcccgcttga cgatgttgt                                              19

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 30
aactcctgct gcattcccac caa                                         23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 31
ctccacagcc caacagaatg act                                         23

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aggcctccgg aggaaccggc tgcccatgcc aact                             34

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: modified_base
<222> LOCATION: (19)
<223> OTHER INFORMATION: a, c, t, g, other or unknown

<400> SEQUENCE: 33
aggcctccgg aggaaccgnc tgcccatgcc aact                             34

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atcattgctc cctctggcta tcatgccaac t                                31

<210> SEQ ID NO 35
<211> LENGTH: 30
<212> TYPE: DNA
```

```
-continued

<213> ORGANISM: Artificial Sequence
<220> FEATURE:
<223> OTHER INFORMATION: Description of Artificial Sequence: Synthetic
      oligonucleotide

<400> SEQUENCE: 35
atcattgctc cctctggtta tcatgccaac                                          30
```